United States Patent
Johnson

(10) Patent No.: US 7,547,304 B2
(45) Date of Patent: Jun. 16, 2009

(54) GUIDEWIRE-CENTERING CATHETER TIP

(75) Inventor: Eric G. Johnson, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/324,714

(22) Filed: Dec. 19, 2002

(65) Prior Publication Data

US 2004/0122415 A1 Jun. 24, 2004

(51) Int. Cl.
*A61M 25/00* (2006.01)
(52) U.S. Cl. ....................................... 604/528
(58) Field of Classification Search ............ 604/164.01, 604/164.12–165.04, 523, 528, 510, 524, 604/525; 600/3, 585, 434; 606/200
See application file for complete search history.

(56) References Cited

U.S. PATENT DOCUMENTS

| | | | | |
|---|---|---|---|---|
| 3,402,717 A | * | 9/1968 | Doherty | 128/207.15 |
| 4,488,548 A | * | 12/1984 | Agdanowski | 128/204.25 |
| 4,955,862 A | * | 9/1990 | Sepetka | 604/164.13 |
| 5,122,125 A | | 6/1992 | Deuss | 604/282 |
| 5,336,192 A | | 8/1994 | Palestrant | 604/167 |
| 5,593,394 A | * | 1/1997 | Kanesaka et al. | 604/524 |
| 5,607,404 A | | 3/1997 | Khairkhahan | 604/264 |
| 5,690,641 A | * | 11/1997 | Sorensen et al. | 606/107 |
| 5,863,284 A | | 1/1999 | Klein | 600/3 |
| 5,885,508 A | | 3/1999 | Ishida | |
| 5,919,162 A | * | 7/1999 | Burns | 604/99.01 |
| 6,071,227 A | | 6/2000 | Popowski et al. | 600/3 |
| 6,074,338 A | | 6/2000 | Popowski et al. | 600/3 |
| 6,196,963 B1 | | 3/2001 | Williams | 600/3 |
| 6,228,110 B1 | * | 5/2001 | Munsinger | 623/1.12 |
| 6,302,875 B1 | * | 10/2001 | Makower et al. | 604/528 |
| 6,403,011 B1 | | 6/2002 | Stamberg | 264/400 |
| 6,432,091 B1 | | 8/2002 | Davey | 604/246 |
| 6,454,737 B1 | | 9/2002 | Nita et al. | 604/22 |
| 2002/0058963 A1 | | 5/2002 | Vale et al. | 606/200 |
| 2002/0077586 A1 | * | 6/2002 | Madsen et al. | 604/27 |
| 2002/0120286 A1 | | 8/2002 | DoBrava et al. | 606/200 |
| 2003/0092956 A1 | * | 5/2003 | Williams | 600/1 |
| 2004/0006361 A1 | * | 1/2004 | Boyle et al. | 606/200 |

FOREIGN PATENT DOCUMENTS

EP 1493403 1/2005
WO 02/11808 2/2002

* cited by examiner

*Primary Examiner*—Kevin C Sirmons
*Assistant Examiner*—Catherine N Witczak
(74) *Attorney, Agent, or Firm*—Wayne D. House

(57) ABSTRACT

A catheter for use with a guidewire, the catheter having a distal tip that centers the guidewire even when the catheter is severely bent, thereby avoiding protrusion of the distal tip of the catheter at the outer meridian of the catheter bend and reducing the risk of the catheter tip catching on the luminal surface of the adjacent vasculature. The distal tip of the catheter incorporates at least one guidewire bearing, preferably multiple bearings in the form of longitudinally oriented ribs, which provide the centering characteristic with minimal friction between the inner surface of the catheter distal tip and the outer surface of the guidewire. Preferably, at least four guidewire bearings are provided.

26 Claims, 6 Drawing Sheets

GUIDEWIRE-CENTERING CATHETER TIP

FIELD OF THE INVENTION

The present invention relates to the field of catheters intended for use with guidewires, and more particularly to the distal tip of such catheters.

BACKGROUND OF THE INVENTION

Catheters intended for use with guidewires have a distal tip with an inner diameter that is slightly larger than the outside diameter of the intended guidewire. The difference in diameter is necessary to provide the guidewire with operating clearance. When navigating tortuous anatomy or crossing a previously deployed stent, the guidewire is not concentric with the distal tip of the catheter due to this required clearance. Because of this required clearance, the distal tip of the catheter protrudes along the outer meridian of a severely bent catheter/guidewire assembly, with the result that it is at risk of catching on the vessel wall and consequently impede trackability of the catheter over the guidewire. This can result in an increase in the time of the procedure as the medical practitioner may be forced to withdraw the catheter and again attempt to maneuver the assembly through the tortuous anatomy responsible for the severe bend. Likewise, if the catheter tip catches on the luminal surface of the vessel wall, damage to the luminal surface may result, requiring surgical intervention. Similarly, the catheter tip is also at risk of catching on the struts at the end of a previously deployed stent, thereby impeding crossability.

There have been various catheter designs in the art that describe centering concepts that relate to the tip of the catheter. U.S. Pat. No. 5,122,125 to Deuss teaches a guiding catheter having a tip portion with external ribs intended to center the catheter within the vessel it is being moved through. U.S. Pat. No. 6,228,110 to Munsinger describes a catheter with a tip portion including a series of bristles affixed to the luminal surface of the tip. The bristles are intended to serve as an axial brake designed to inhibit unintended axial motion between the catheter and a guidewire within the catheter. The concentric design of the bristles serves to center the guidewire within the catheter tip. However, the group of bristles are located some distance proximally from the distal end of the catheter, with the result that while an effective axial braking means is provided between the catheter and guidewire, the guidewire is not centered as it exits the distal end of the catheter.

SUMMARY OF THE INVENTION

The present invention relates to centering means provided to the distal tip of a catheter to assure that a guidewire or other device exiting the distal tip is substantially centered with respect to the distal tip, thereby reducing any risk of the edge of the catheter tip catching on the luminal surface of a vessel when the tip region of the catheter is severely bent, as is often the case when traversing tortuous vessels with the catheter.

The centering means comprises at least one and preferably multiple bearing surfaces located on the luminal surface of the catheter tip. These bearing surfaces preferably take the form of ribs that project inwardly from the luminal surface of the catheter tip, the ribs preferably being oriented substantially parallel to the longitudinal axis of the catheter. They are preferably integrally formed on the luminal surface of the catheter tip and consequently are from the same material that comprises the catheter tip. Preferably, at least three, and more preferably at least four, such ribs are provided, equally spaced around the luminal surface of the catheter tip.

To ensure optimal centering, these "bearings" can be formed to provide a slight interference with a guidewire or other device intended to be passed through the lumen of the catheter. The interference is of such a minimal amount that no perceptible increase in friction between the guidewire and catheter occurs.

The bearings, particularly when they take the form of longitudinally-oriented ribs, are preferably of a relatively short length, extending back into the catheter from the distal tip for a length of, for example, about 6 mm or less, and may be as short as 3 mm or less. The proximal ends of the bearings preferably transition smoothly rather than abruptly into the luminal surface of the catheter. In transverse cross section, the ribs preferably have a semi-circular shape.

The catheter tip of the present invention can be used with any catheter that is placed with a guidewire of any size. Possible applications include, but are not limited to, cardiology catheters (which are typically placed over guidewires of about 0.36 mm diameter), urology catheters (typically placed over guidewires of about 0.89 mm diameter) and radiology catheters (typically placed over guidewires of about 0.97 mm diameter).

While it is preferred that the bearings take the form of ribs, other forms may be used such as hemispherical bumps or an annular ring placed at the luminal surface of the catheter tip.

DETAILED DESCRIPTION OF THE INVENTION

Figure 1:
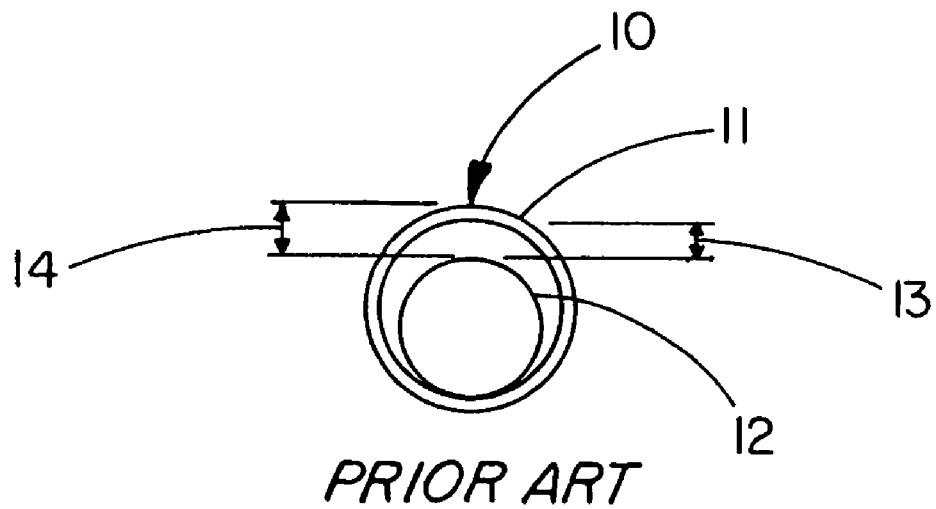
FIG. 1 is a transverse cross section of a catheter distal tip and guidewire of the prior art.
Figure 2:
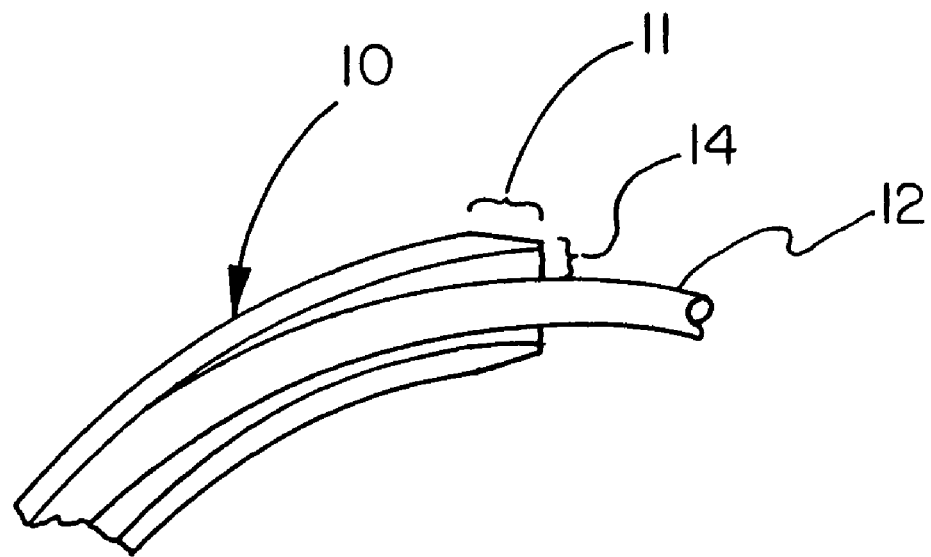
FIG. 2 is a side view of a catheter and guidewire of FIG. 1, showing the catheter in a bent state and showing the resulting "ledge" at the catheter tip where the guidewire exits.

FIG. 1 is a typical transverse cross section of the tip portion 11 of a catheter 10 of the prior art. A device such as a guidewire 12 is contained within the lumen of the catheter 10. There is provided clearance, shown as dimension 13, between the inside diameter of the tip portion 11 and the outside diameter of the guidewire 12. As further described by the side view of FIG. 2, when the catheter 10 is severely bent as is often the case when traversing tortuous vessels with the catheter 10 and guidewire 12, the guidewire will offset to the inner meridian of the bent catheter 10. The result is that a ledge 14 is created by the wall thickness of the tip portion 11 of the catheter 10 in combination with the operating clearance 13 between the guidewire 12 and inside diameter of the tip portion 11. It is this ledge 14 that poses a risk of catching on the luminal surface of the vasculature.

Figure 3:
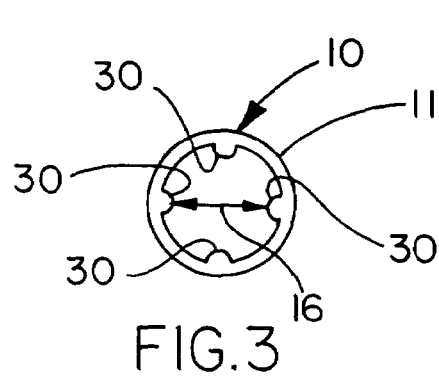
FIG. 3 is a transverse cross section of a catheter tip of the present invention showing bearings projecting from the luminal surface of the catheter tip.

FIG. 3 describes a transverse cross section of a tip portion 11 of a catheter 10 of the present invention. Projecting from the luminal surface of the tip portion 11 are multiple bearings 30, serving as centering means for any device, such as a guidewire 12, exiting the tip portion 11. These bearings 30 are preferably located only in the region of the tip portion 11, with result that the operating clearance between the device and the luminal surface of the catheter 10 is maintained over the remainder of the length of the catheter 10.

Bearings 30 can be formed to provide a slight interference with a guidewire or other device intended to be passed through the lumen of the catheter. For example, an inside diameter of the catheter tip as measured between two opposing bearings, shown as inside diameter 16, may interfere in an amount of about 0.025 to 0.050 mm with the outside diameter of the intended guidewire. The interference is of such a minimal amount that no perceptible increase in friction between the guidewire and catheter occurs.

Figure 3A:
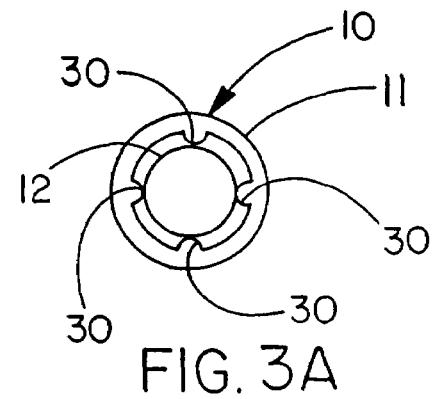
FIG. 3A is a transverse cross section of the catheter tip of FIG. 3 further showing a device such as a guidewire centered within the catheter tip.

FIG. 3A is a transverse cross section of the catheter tip 11 of FIG. 3 further showing a device such as guidewire 12 centered within catheter tip 11.

While four bearings 30 are shown, it is apparent that at least three are required. At least four are preferred, and more than four may be used, such as five, six, seven, eight, nine, ten, etc.

The transverse cross section of FIG. 3A includes a device such as guidewire 12 shown centered with bearings 30. In a preferred embodiment, there is a slight interference fit between opposing bearings 30 and guidewire 12. Typically, the inside diameter of the catheter tip portion 11 as measured between opposing bearings 30 will be slightly less than the outside diameter of guidewire 12. For example, for a guidewire having an outside diameter of about 0.36 mm (a typical cardiology catheter), the inside diameter of tip portion 11 as measured between opposing bearings 30 will preferably be about 0.31 mm.

Figure 4:
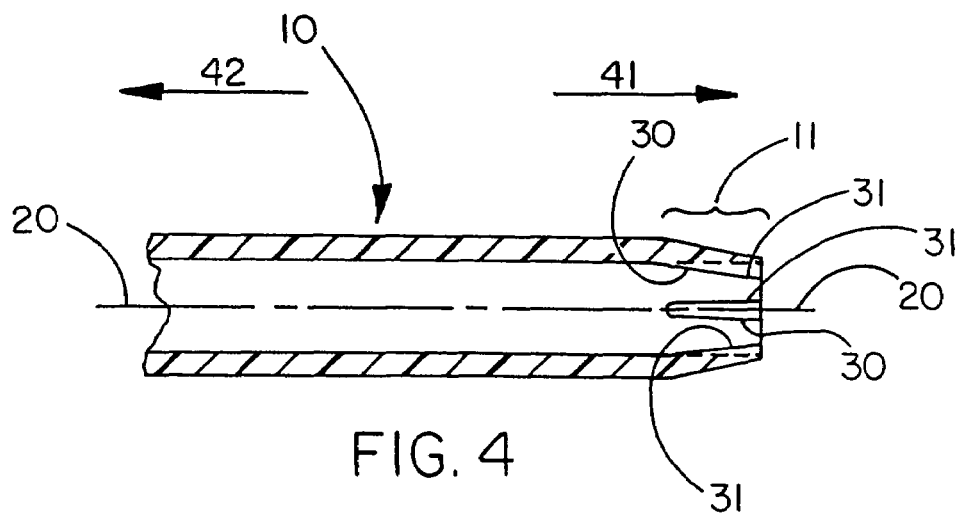
FIGS. 4 and 4A are longitudinal cross sections of catheter tips of the present invention, showing the bearings in the form of ribs oriented parallel to the longitudinal axis of the catheter.

The longitudinal cross section of FIG. 4 shows a preferred embodiment wherein bearings 30 take the form of longitudinally-oriented ribs 31, substantially parallel to the longitudinal axis 20 of catheter 10. The distal end of the catheter 10 is indicated by arrow 41 and the proximal end is indicated by arrow 42. These ribs 31 are preferably of a length that limits them to the tip portion 11 of the catheter 10. A typical length for ribs extending for the full length of the tip portion 11 would be about 3 mm. While their height (as measured perpendicularly from the luminal surface) is maximized at the very distal end of the tip portion 11, they preferably merge into the luminal surface of the catheter 10 at their proximal end.

Figure 4A:
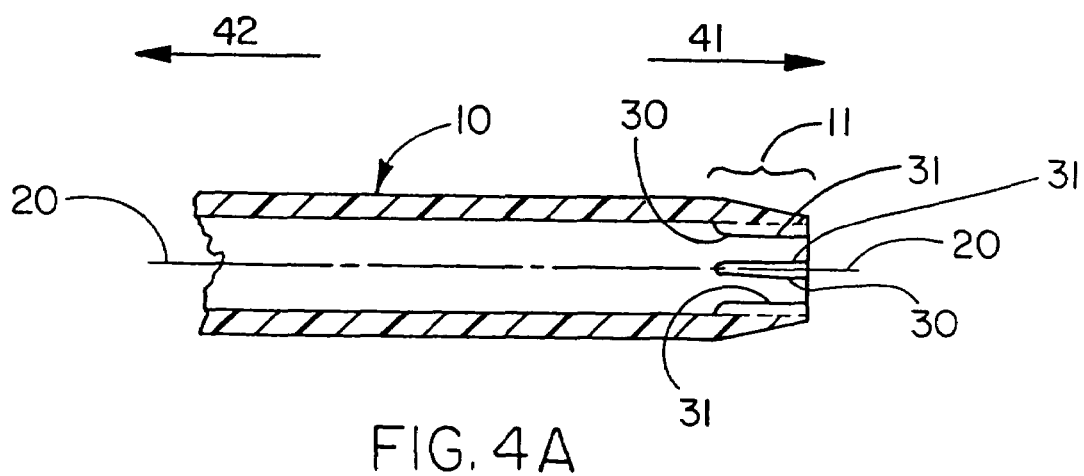

Alternatively, as shown by the longitudinal cross section of FIG. 4A, the height of the bearings 30 may be kept substantially constant along the full length of each bearing, so that each bearing 30 exerts a relatively uniform force along its entire length against a guidewire or other device inserted through the catheter tip 11.

While the distal end of tip portion 11 is shown to be square, that is, cut off so as to be perpendicular to the longitudinal axis 20 of the catheter 10, it may be made with various shapes. It is believed that the end should most preferably be round in longitudinal cross section.

Figure 5:
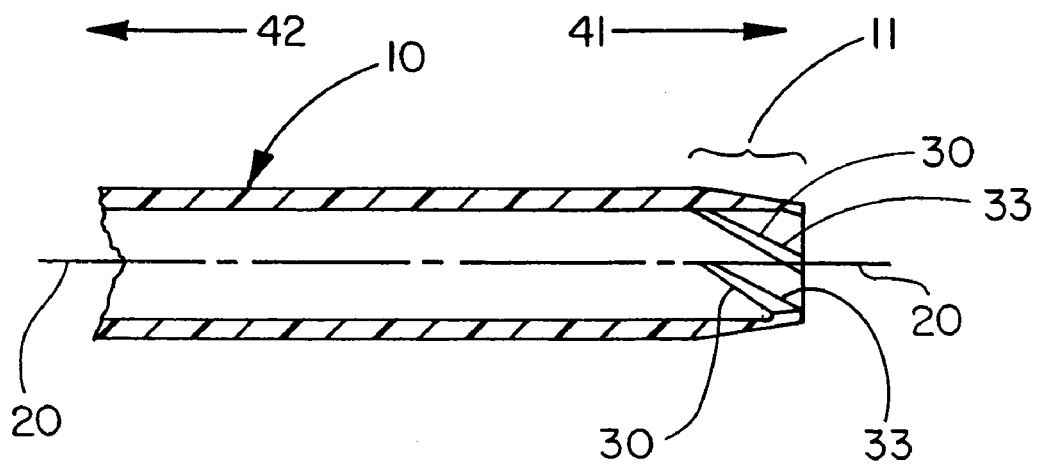
FIG. 5 is a longitudinal cross section of a catheter tip of the present invention, showing the bearings in the form of ribs oriented helically with respect to the longitudinal axis of the catheter.
Figure 6:
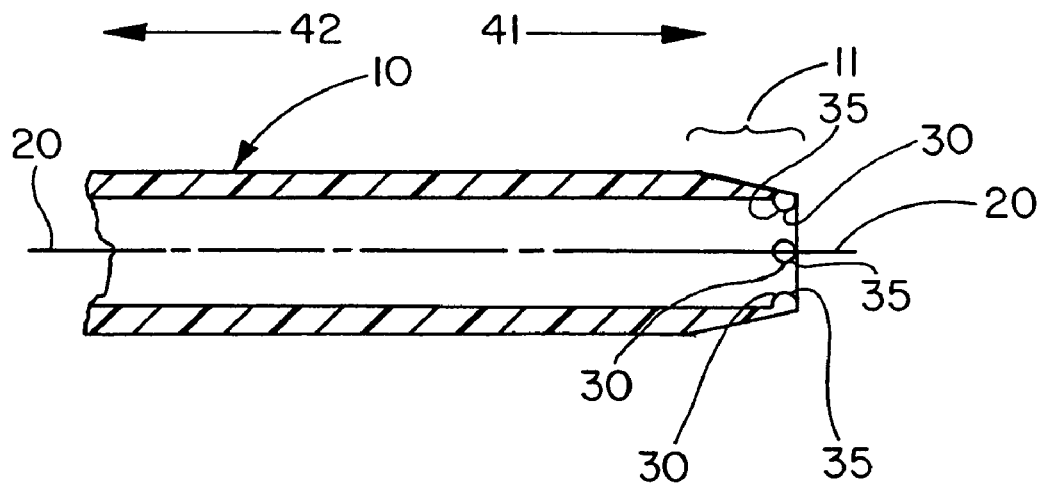
FIG. 6 is a longitudinal cross section of a catheter tip of the present invention, showing the bearings in the form of hemispheres located at the tip of the catheter.

In another embodiment shown in the longitudinal cross section of FIG. 5, the bearings may take the form of ribs oriented other than longitudinally, such as helically-oriented ribs 33. The longitudinal cross section of FIG. 6 shows still another alternative wherein bearings are in the form of small protrusions 35 of hemispherical or substantially hemispherical shape, located at the very distal end of tip portion 11. It is apparent that various shapes may be used for the protruding bearing surfaces.

Figure 7:
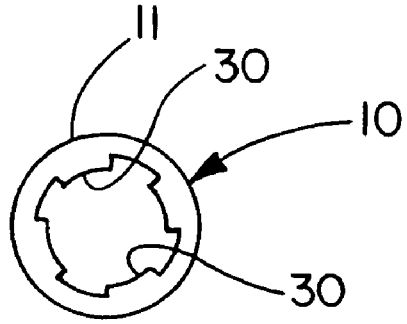
FIG. 7 is a transverse cross section of an alternative embodiment of the catheter tip.

FIG. 7 describes a transverse cross section of an alternative embodiment of the catheter tip 11 wherein the bearings 30 are not of rounded cross section. Rather, the bearings 30 in this instance are of a shape that provides a larger contact area against the surface of the centered device.

Figure 8:
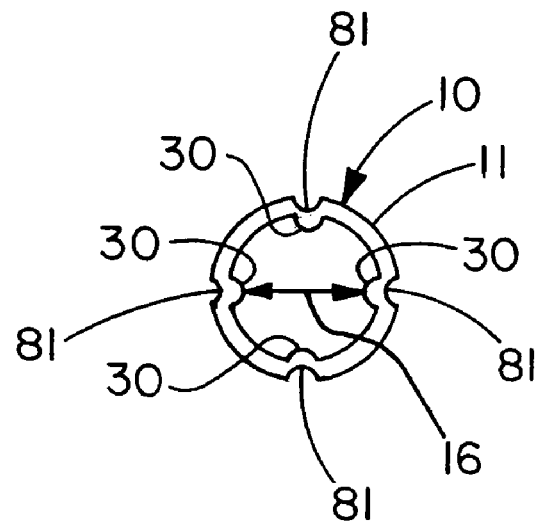
FIG. 8 is a transverse cross section of another alternative embodiment in the form of a variation of the tip described in FIG. 3.

FIG. 8 shows a transverse cross section of the catheter tip 11 representing a variation of the embodiment described by the transverse cross section of FIG. 3. FIG. 8 describes relieved areas 81 on the exterior surface of the catheter tip that are directly opposite the bearings 30 on the luminal surface. These relieved areas 81 reduce the resistance of the bearings and allow for a more flexible and less rigid catheter tip 11.

The bearings are preferably integral to the luminal surface of the catheter tip, being molded as a part of that surface during the manufacture of the catheter tip. The catheter including the tip with bearings can be fabricated of various materials and combinations of materials known to those of skill in the art of catheters, using methods known in this art. These materials include polymers such as amide-based thermoplastic elastomers, silicones, polyurethanes, polyamides and various fluorinated polymers including polytetrafluoroethylene and fluorinated ethylene propylene. Materials of particular durometer may be selected according to the degree of flexibility or rigidity desired. The catheter tubing may be reinforced with materials such as braided wires embedded in the catheter wall.

Figure 9:
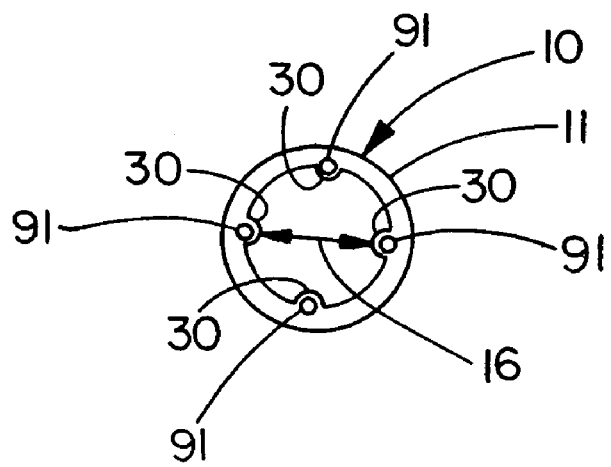
FIG. 9 is a transverse cross section of an alternative embodiment wherein wires are embedded in the material of the catheter tip and bearing.

Alternatively, the bearings may be separately affixed if desired, by, for example, the use of adhesives suitable for the materials involved and for the medical use. This offers the possibility of providing bearings that have a different degree of flexibility (or rigidity) from the material of the remainder of the catheter tip. For example, bearings may be made of individual, relatively short pieces of metal wire for additional tip rigidity and/or radiopacity. The wire can be exposed as the actual bearing surface. Alternatively, as shown in the transverse cross section of FIG. 9, wires 91 may be embedded in the material of the catheter tip if it is preferred that the exposed bearing surface is the same material as that of the catheter tip.

Figure 10:
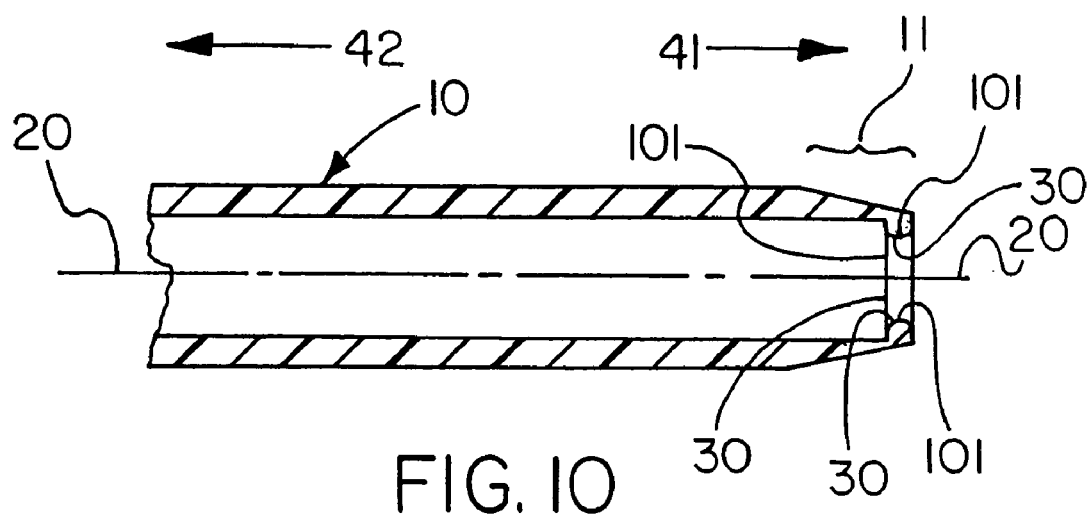
FIGS. 10 and 11 are longitudinal and transverse cross sections respectively of an alternative embodiment wherein a single bearing surface in the form of a circumferentially oriented raised ring-shaped bearing surface, located at the luminal surface of the distal tip of the catheter.
Figure 11:
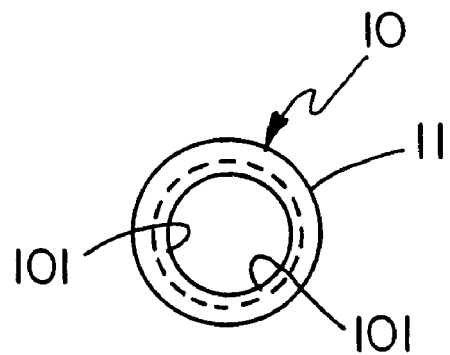

FIGS. 10 and 11 describe longitudinal and transverse cross sections respectively of an alternative embodiment wherein a single bearing surface in the form of a circumferentially oriented raised ring-shaped bearing surface 101, located at the luminal surface of the distal tip of the catheter. While the longitudinal cross section shows a semi-circular profile for the bearing surface, it is apparent that other shapes may also be used. While the ring may be continuous around the entire circumference of the luminal surface, it is apparent that the ring may be interrupted as with notches to render it into two or more circumferentially oriented bearing surfaces.

Figure 12A:
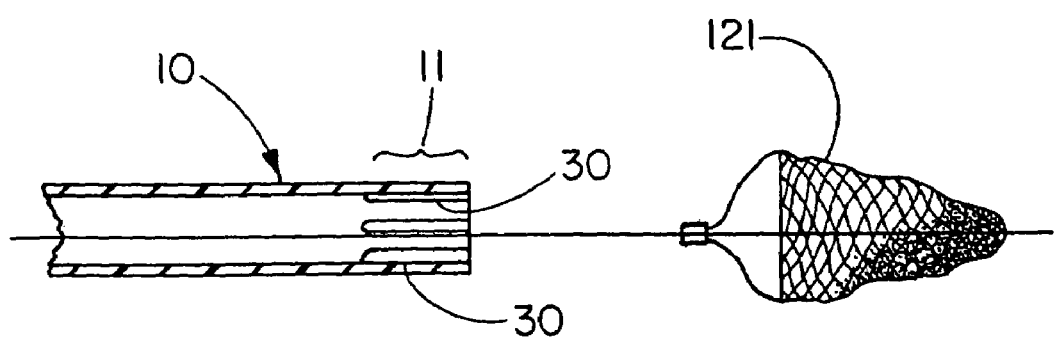
FIGS. 12A and 12B describe sequential side views of the catheter tip, with the tip shown in cross section, as used to capture and collapse an embolic filter.
Figure 12B:
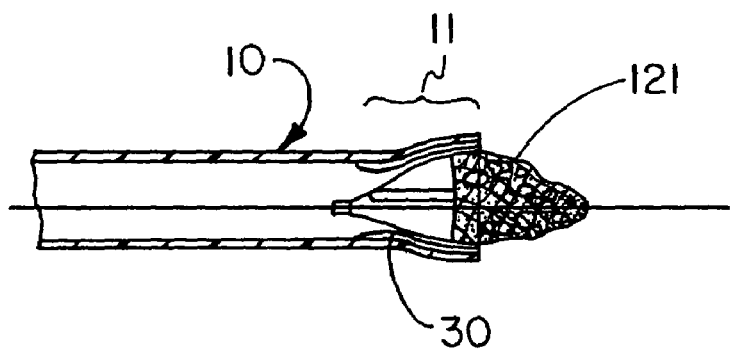

FIGS. 12A and 12B describe sequential side views of the catheter tip (with the catheter 10 and tip 11 shown in cross section) as used to capture and collapse an embolic filter 121. For this application, the catheter tip 11 is made from an elastomeric material such as silicone, which allows the catheter tip portion 11 to slightly increase in diameter by stretching to accommodate the capture and collapse of the embolic filter 121 as shown. The tip aids in collapsing the filter 121 to a smaller size for removal from the vasculature and ensures that material captured in filter 121 is also withdrawn via the catheter 10. Bearings 30 are preferably of a more rigid material than the catheter tip 11, providing column strength that prevents the tip 11 from rolling inward and buckling.

While the principles of the invention have been made clear in the illustrative embodiments set forth herein, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

I claim:

1. A catheter assembly comprising a catheter tube having a lumen, a longitudinal axis, a length, a luminal surface, a tip portion located at a very distal tip of the catheter assembly, said tip portion having a distal end that is substantially perpendicular to the longitudinal axis of the catheter tube, and a device at least partially contained within and movable through the lumen of the entire length of the catheter tube, said catheter tube having centering means projecting from the luminal surface of only the tip portion wherein a distal-most portion of said centering means is coplanar with the distal end of the catheter tube, said centering means arranged such that when the device is moved through the lumen of the catheter tube the device remains substantially centered relative to the tip portion at the very distal tip of the catheter assembly as it emerges from the tip portion of the catheter tube when the tip portion of the catheter tube is in a bent state, the centering means having an inside diameter slightly smaller than the outside diameter of the device, and wherein said centering means and said tip portion are integrally formed of one material.

2. A catheter assembly according to claim 1 wherein the centering means comprise at least four bearing surfaces projecting from the luminal surface of the tip portion of the catheter tube.

3. A catheter assembly according to claim 1 wherein the centering means comprise multiple longitudinally-oriented ribs projecting from the luminal surface of the tip portion of the catheter tube.

4. A catheter assembly according to claim 1 wherein the centering means comprise multiple helically-oriented ribs projecting from the luminal surface of the tip portion of the catheter tube.

5. A catheter assembly according to claim 1 wherein the centering means comprise multiple substantially hemispherical shapes projecting from the luminal surface of the tip portion of the catheter tube.

6. A catheter assembly according to claim 1 wherein the centering means extends back into the catheter tube from the very distal tip for a length of 6 mm or less.

7. A catheter assembly according to claim 1 wherein the device comprises a guidewire.

8. A catheter assembly according to claim 1 wherein the device comprises an embolic filter.

9. A catheter assembly comprising a catheter tube having a lumen, a longitudinal axis, a length, a luminal surface, a tip portion located at a very distal tip of the catheter assembly, said tip portion having a distal end that is substantially perpendicular to the longitudinal axis of the catheter tube, and a device at least partially contained within and movable through the lumen of the entire length of the catheter tube, said catheter tube having centering means projecting from the luminal surface of only the tip portion, wherein a distal-most portion of said centering means is coplanar with the distal end of the catheter tube, said centering means arranged such that when the device is moved through the lumen of the catheter tube the device remains substantially centered relative to the tip portion at the very distal tip of the catheter assembly as it emerges from the tip portion of the catheter tube when the tip portion of the catheter tube is in a bent state, and wherein said centering means and said tip portion are integrally formed of one material.

10. A catheter assembly according to claim 9 wherein the centering means comprise at least four bearing surfaces projecting from the luminal surface of the tip portion of the catheter tube.

11. A catheter assembly according to claim 9 wherein the centering means comprise multiple longitudinally-oriented ribs projecting from the luminal surface of the tip portion of the catheter tube.

12. A catheter assembly according to claim 9 wherein the centering means comprise multiple helically-oriented ribs projecting from the luminal surface of the tip portion of the catheter tube.

13. A catheter assembly according to claim 9 wherein the centering means comprise multiple substantially hemispherical shapes projecting from the luminal surface of the tip portion of the catheter tube.

14. A catheter assembly according to claim 9 wherein the centering means extends back into the catheter tube from the very distal tip for a length of 6 mm or less.

15. A catheter assembly according to claim 9 wherein the device comprises a guidewire.

16. A catheter assembly according to claim 9 wherein the device comprises an embolic filter.

17. A catheter assembly according to claim 9 wherein said centering means extends back into the catheter tube from the very distal tip for a length of 3 mm or less.

18. A catheter tube comprising a tube for insertion into a body of a patient, having a longitudinal axis, a proximal end, a distal end that is substantially perpendicular to the longitudinal axis of the catheter tube, a lumen extending between the proximal and distal ends, and a device at least partially contained within and movable through the lumen of the entire length of the catheter tube a luminal surface, and a distal tip portion located adjacent to the distal end of the catheter tube, said catheter tube having centering means projecting from the luminal surface of only the distal tip portion wherein a distal-most portion of said centering means is coplanar with the distal end of the catheter tube, and wherein said centering means and said tip portion are integrally formed of one material.

19. A catheter tube according to claim 18 wherein the centering means comprise at least four bearing surfaces projecting from the luminal surface of the tip portion of the catheter tube.

20. A catheter tube according to claim 18 wherein the centering means comprise multiple longitudinally-oriented ribs projecting from the luminal surface of the tip portion of the catheter tube.

21. A catheter tube according to claim 18 wherein the centering means comprise multiple helically-oriented ribs projecting from the luminal surface of the tip portion of the catheter tube.

22. A catheter tube according to claim 18 wherein the centering means comprise multiple substantially hemispherical shapes projecting from the luminal surface of the tip portion of the catheter tube.

23. A catheter tube according to claim 18 wherein the centering means extends back into the catheter tube from the very distal tip for a length of 6 mm or less.

24. A catheter tube according to claim 18 wherein said centering means extends back into the catheter tube from the very distal tip for a length of 3 mm or less.

25. A catheter tube according to claim 18 wherein the device comprises a guidewire.

26. A catheter tube according to claim 18 wherein the device comprises an embolic filter.

* * * * *